United States Patent [19]

Fernandes et al.

[11] Patent Number: 5,542,012

[45] Date of Patent: Jul. 30, 1996

[54] MULTI-FUNCTIONAL PHOTOMETER WITH MOVABLE LINKAGE FOR ROUTING OPTICAL FIBERS

[75] Inventors: Jorge Fernandes, San Francisco; Michael C. Norris, Los Gatos, both of Calif.

[73] Assignee: Molecular Dynamics, Sunnyvale, Calif.

[21] Appl. No.: 373,408

[22] Filed: Jan. 17, 1995

Related U.S. Application Data

[62] Division of Ser. No. 100,541, Jul. 30, 1993, Pat. No. 5,436,718.

[51] Int. Cl.$^6$ .................................................. G02B 6/26
[52] U.S. Cl. .............................. 385/25; 385/15; 385/16; 385/24; 385/22
[58] Field of Search .................................. 385/15, 16, 24, 385/25, 18, 19, 20, 21, 22, 59; 356/73, 318, 417, 418, 436, 440; 250/227.23, 227.26, 458.1, 459.1, 461.1, 462.2

[56] References Cited

U.S. PATENT DOCUMENTS

| | | | |
|---|---|---|---|
| 3,697,185 | 10/1972 | Kassel et al. | 356/181 |
| 3,874,780 | 4/1975 | Love | 385/15 X |
| 4,223,978 | 9/1980 | Kummer et al. | 385/22 X |
| 4,303,302 | 12/1981 | Ramsey et al. | 385/22 X |
| 4,373,779 | 2/1983 | Dorsey | 585/25 X |
| 4,415,229 | 11/1983 | McCullough | 385/22 |
| 4,477,190 | 10/1984 | Liston et al. | 356/418 |
| 4,501,970 | 2/1985 | Nelson | 250/458.1 |
| 4,587,812 | 5/1986 | Brega | 66/232 |
| 4,622,468 | 11/1986 | Stefanski et al. | 250/458.1 |
| 4,626,684 | 12/1986 | Landa | 250/328 |
| 4,669,878 | 6/1987 | Meier | 356/319 |
| 4,730,922 | 3/1988 | Bach et al. | 356/73 |
| 4,750,837 | 6/1988 | Gifford et al. | 356/417 |
| 4,799,756 | 1/1989 | Hirschfeld | 385/33 X |
| 4,802,768 | 2/1989 | Gifford et al. | 356/417 |
| 4,815,812 | 3/1989 | Miller | 385/25 X |
| 4,820,045 | 4/1989 | Boisde et al. | 356/319 |
| 4,840,485 | 6/1989 | Gratton | 356/317 |
| 4,896,935 | 1/1990 | Lee | 385/22 X |
| 4,937,457 | 6/1990 | Mitchell | 250/458.1 |
| 4,945,245 | 7/1990 | Levin | 250/461.2 |
| 4,968,148 | 11/1990 | Chow et al. | 356/427 |
| 5,030,832 | 7/1991 | Williams et al. | 250/458.1 |
| 5,125,747 | 6/1992 | Sayegh et al. | 356/407 |
| 5,131,746 | 7/1992 | O'Rourke et al. | 356/319 |
| 5,141,609 | 8/1992 | Sweedler et al. | 204/180.1 |
| 5,143,853 | 9/1992 | Walt | 436/501 |
| 5,151,869 | 9/1992 | Alcala | 364/497 |
| 5,214,727 | 5/1993 | Carr et al. | 385/22 |
| 5,353,363 | 10/1994 | Keck et al. | 385/25 X |
| 5,436,718 | 7/1995 | Fernandes et al. | 356/73 |

FOREIGN PATENT DOCUMENTS 0062160  10/1982  European Pat. Off. ............ 385/12 X

OTHER PUBLICATIONS

Video Tape Entitled "THE CYTOFLUOR FLUORESCENCE MEASUREMENT SYSTEM–AUTOMATED FLUORESCENCE SCANNING" Millipore, 1990 (previously submitted in parent file).
PCT International Search Report for International Application No. PCT/US/94/06894, Aug. 25, 1995.
PCT International Written Opinion for International Application No. PCT/US/94/06894, Mar. 14, 1995.

Primary Examiner—Brian Healy
Attorney, Agent, or Firm—Blakely, Sokoloff, Taylor & Zafman

[57] ABSTRACT

A multi-functional photometer includes a scanning mechanism having a housing (10) that bears a movable linkage (12). The linkage is coupled to an optical scanning head (18) and incorporates optical fibers for transmitting radiant energy to and from the scanning head. The arm comprises a C-shaped "elbow" member (14), pivotally attached to a "shoulder" member (16). In turn, the "shoulder" member of the arm is pivotally connected to the housing. Dynamic couplings join the optical fibers such that the shapes thereof remain fixed regardless of the orientation of the arm. The housing further incorporates a Cartesian-coordinate table (20) for positioning the scanning head with respect to a microplate (22) that contains a plurality of analyte samples.

10 Claims, 10 Drawing Sheets

MULTI-FUNCTIONAL PHOTOMETER WITH MOVABLE LINKAGE FOR ROUTING OPTICAL FIBERS

This is a divisional of application Ser. No. 08/100,541, filed Jul. 30, 1993, now U.S. Pat. No. 5,436,718.

FIELD OF THE INVENTION

The present invention relates to the field of spectroscopy, particularly to a multi-functional photometer capable of measuring light absorbance, fluorescence, and luminescence of a sample.

BACKGROUND OF THE INVENTION

In biological research, it is often necessary to assay samples for content of various chemicals, hormones, and enzymes. Spectroscopy, which is the measurement and interpretation of electromagnetic radiation absorbed or emitted when the molecules, or atoms, of a sample move from one energy state to another, is widely utilized for this purpose. Currently, the most common spectroscopic techniques pertain to measurements of absorbance, fluorescence, and luminescence.

Chemical analyses with absorption spectroscopy allow one to determine concentrations of specific components, to assay chemical reactions, and to identify individual compounds. Absorbance measurements are most commonly used to find the concentration of a specific composition in a sample. According to Beer's law, for a composition that absorbs light at a given wavelength, the total absorbed quantity of such light is related to the quantity of that composition in the sample.

Fluorescence, in turn, is a physical phenomenon based upon the ability of some substances to absorb and subsequently emit electromagnetic radiation. The emitted radiation has a lower energy level and a longer wavelength than the excitation radiation. Moreover, the absorption of light is wavelength dependent. In other words, a fluorescent substance emits light only when the excitation radiation is in the particular excitation band (or bands) of that substance.

For fluorescence measurements, fluorescent dyes called fluorophores are often used to "tag" molecules of interest, or targets. After being irradiated by an excitation beam, fluorophores, bonded to the targets, emit light that is then collected and quantized. The ratio of the intensity of the emitted fluorescent light to the intensity of the excitation light is called the "relative fluorescence intensity" and serves as an indicator of target concentration. Another useful characteristic is the phase relationship between the cyclic variations in the emitted light and the variations in the excitation light, i.e., the time lag between corresponding variations in the emission and excitation beams.

As noted above, luminescence measurements can also be employed for analyzing biological samples. Luminescence is the property of certain chemical substances to emit light as a result of a chemical change; no excitation from a light source is necessary. Moreover, luminescence can be produced by energy-transfer mechanisms that take energy of a high intensity, e.g., a radioactive emission, and transform it to energy of a low intensity, e.g., a flash of light.

At the present time, a variety of spectroscopic instruments is commonly used in the art. A number of these instruments are designed to be utilized in conjunction with multi-site analyte receptacles called "microplates", which usually comprise one-piece structures having multiplicities of wells for holding analyte samples. Microplates are beneficial since they allow simultaneous preparation of a large number of test samples. Moreover, microplates are inexpensive, safe, sturdy, and convenient to handle. They are also disposable and can be cleaned easily when necessary.

One instrument currently available for fluorescent analysis of samples in microplate wells is the Cytofluor 2300 fluorometer, distributed by Millipore Corporation, Bedford, Mass. This fluorometer includes a scanning head that resides underneath the microplate and moves along the bottom face thereof to scan the sample sites. The scanning head interfaces with the optical system of the device via a bundle of optical fibers that transmits excitation and emission radiation.

However, the capabilities of the Cytofluor 2300 fluorometer are limited in that it cannot perform absorbance measurements. Furthermore, the movement of the scanning head from one microplate well to another continuously alters the geometrical configuration of the optical-fiber bundle that is attached to the head. Consequently, curvatures of the light-transmitting fibers change, introducing variations in their optical properties. These variations create inconsistencies in readings between different wells and adversely affect the repeatability, and thus, accuracy of measurements. Moreover, continuous bending of the fibers produces stresses that cause mechanical failure of the fiber cores.

Additionally, to allow unrestricted movement of the scanning head, flexible plastic fibers are employed, as opposed to less pliable quartz fibers. On the down side, plastic fibers cannot efficiently transmit radiant energy in the ultraviolet (UV) region of the spectrum. Accordingly, the fluorometer is unable to perform measurements, such as binding studies of certain proteins, e.g., tryptophan, since fluorescence analyses of this type require the use of UV radiation. Furthermore, the deformation resistance of the optical-fiber bundle slows the movements of the scanning head, thus limiting the ability of the apparatus to perform kinetic measurements.

Another spectroscopic apparatus utilizing microplates is disclosed in U.S. Pat. No. 4,968,148 to Chow et al., 1990. Chow's device uses an optical distributing element to selectively direct radiant energy to specified microplate sites. One drawback of this instrument is its inability to perform fluorescence measurements. Moreover, the large number of fibers unnecessarily complicates the apparatus and increases production costs. Also, the light-delivery system of the instrument has a fixed geometry that can only accommodate a microplate with one particular well layout. Chow's apparatus does not have the versatility to be utilized with microplates having different configurations of wells.

OBJECTS AND SUMMARY OF THE INVENTION

It is accordingly an object of the invention to provide a multi-functional photometer which overcomes the foregoing disadvantages, e.g., which measures absorbance, fluorescence, and luminescence of a sample; which provides repeatable measurements and produces consistent readings between different test sites; which eliminates recurring bending of optical fibers and mechanical failure thereof; which utilizes optical radiation ranging from the ultraviolet to the infrared spectrum; which is able to carry out kinetic measurements; which can accommodate microplates with different well configurations; and which is relatively simple and inexpensive to manufacture.

Another object of the invention is to supply a photometer having a movable linkage for dynamically and interconnectingly routing optical fibers such that a constant configuration thereof is always maintained during operation of the photometer.

Yet another object of the invention is to provide a photometer which performs analyses of optical signals resulting from phenomena of absorbance, fluorescence, and luminescence over a range of spectral wavelengths. Further objects and advantages will become apparent after consideration of the ensuing description and the accompanying drawings.

In the preferred embodiment of the present invention, a multi-functional photometer includes a scanning mechanism having a housing that bears an articulated movable arm. The arm is coupled to an optical scanning head and incorporates light-transmitting conduits, such as optical fibers, for transmitting radiant energy to and from the scanning head. The arm comprises a C-shaped "elbow" member, pivotally attached to a "shoulder" member. In turn, the "shoulder" member of the arm is pivotally connected to the housing. Dynamic couplings join the optical fibers such that the shapes thereof remain fixed regardless of the orientation of the arm.

The housing further incorporates a Cartesian-coordinate table for positioning the scanning head with respect to a microplate that contains analyte samples. To measure absorbance, fluorescence, and luminescence of the samples, an optical system, incorporating a plurality of lenses, filters, and sensors is utilized. Radiant energy for these measurements is provided by a light source having a microcomputer-controlled power supply. The same microcomputer governs the operation of the optical system and the positioning table.

BRIEF DESCRIPTION OF THE DRAWINGS

The present invention is illustrated by way of example, and not by way of limitation, in the figures of the accompanying drawings, where.

For purposes of illustration, these figures are not necessarily drawn to scale. In all of the figures, like components are designated by like reference numerals.

DETAILED DESCRIPTION

Throughout the following description, specific details, such as materials, dimensions, etc., are set forth in order to provide a more thorough understanding of the invention. However, the invention may be practiced without these particulars. In other instances, well known elements have not been shown or described to avoid unnecessarily obscuring the present invention. Accordingly, the specification and drawings are to be regarded in an illustrative, rather than a restrictive, sense.

Figure 1:
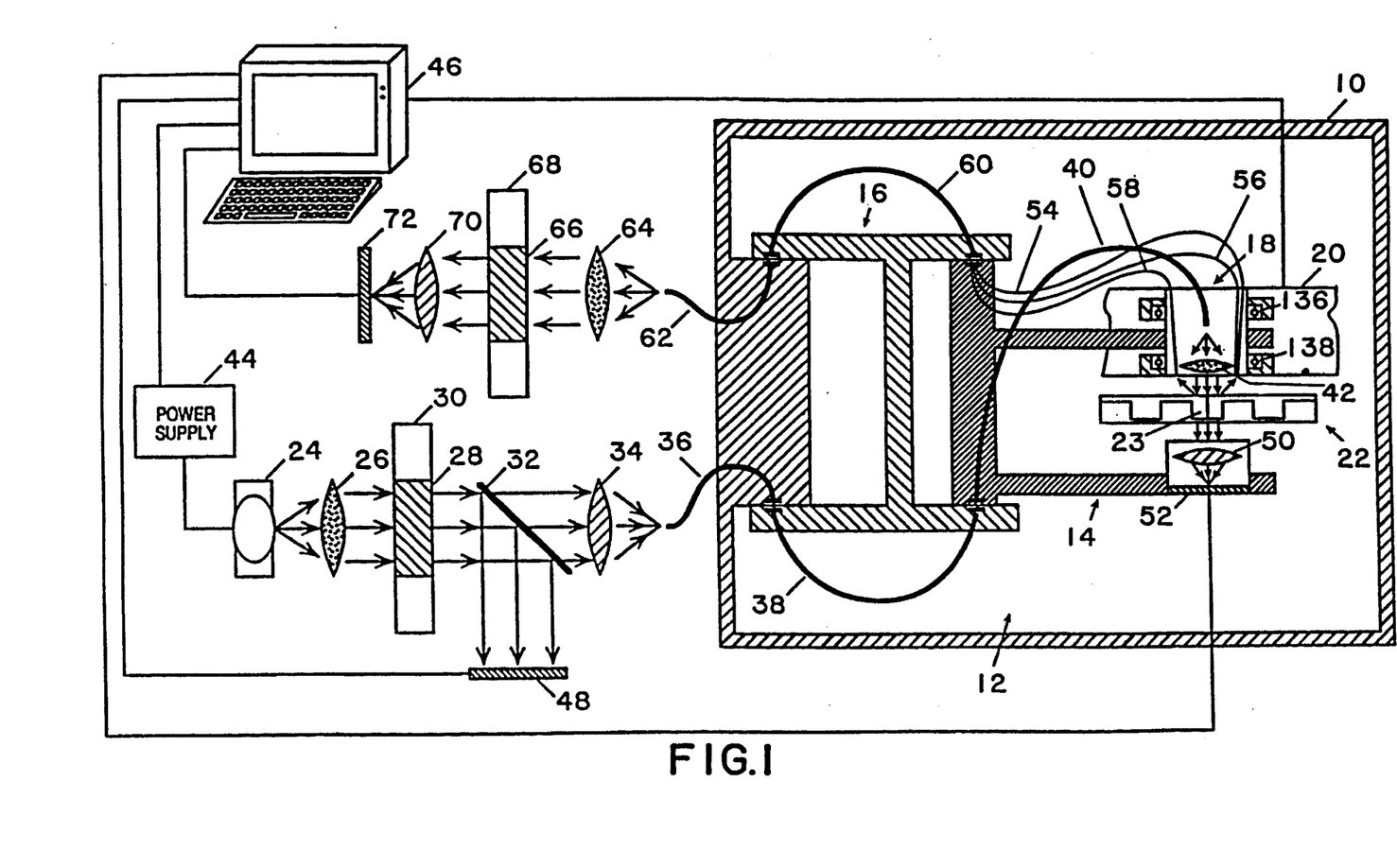
FIG. 1 is a schematic side view of a multi-functional photometer according to the present invention.

FIG. 1 shows a schematic side view of a multi-functional photometer according to the present invention. The photometer comprises a housing 10 that pivotally supports a movable arm 12, containing a C-shaped rigid "elbow" member 14 and a rigid "shoulder" member 16. The housing is approximately 21 cm tall, 18 cm wide, and 26 cm long. Arm 12 incorporates a plurality of optical fibers and is coupled to a first scanning element, e.g., an optical scanning head 18. The structure of arm 12 and the coupling mechanism of the optical fibers will be described fully in the ensuing section of the specification.

Scanning head 18 is rotationally attached through bearings 136 and 138 to a conventional positioning table 20, e.g., the Pen Plotter table, manufactured by Hewlett Packard Company of Palo Alto,. Calif. Positioning tables like the Pen Plotter are often computer controlled such that the computer specifies X and Y coordinates of a point to be located by the mechanism of the table. Table 20 positions head 18 with respect to a microplate 22 that holds samples to be analyzed in a multiplicity of analyte wells, such as a well 23. As illustrated in FIG. 1, both table 20 and microplate 22 are supported within housing 10.

Figure 2:
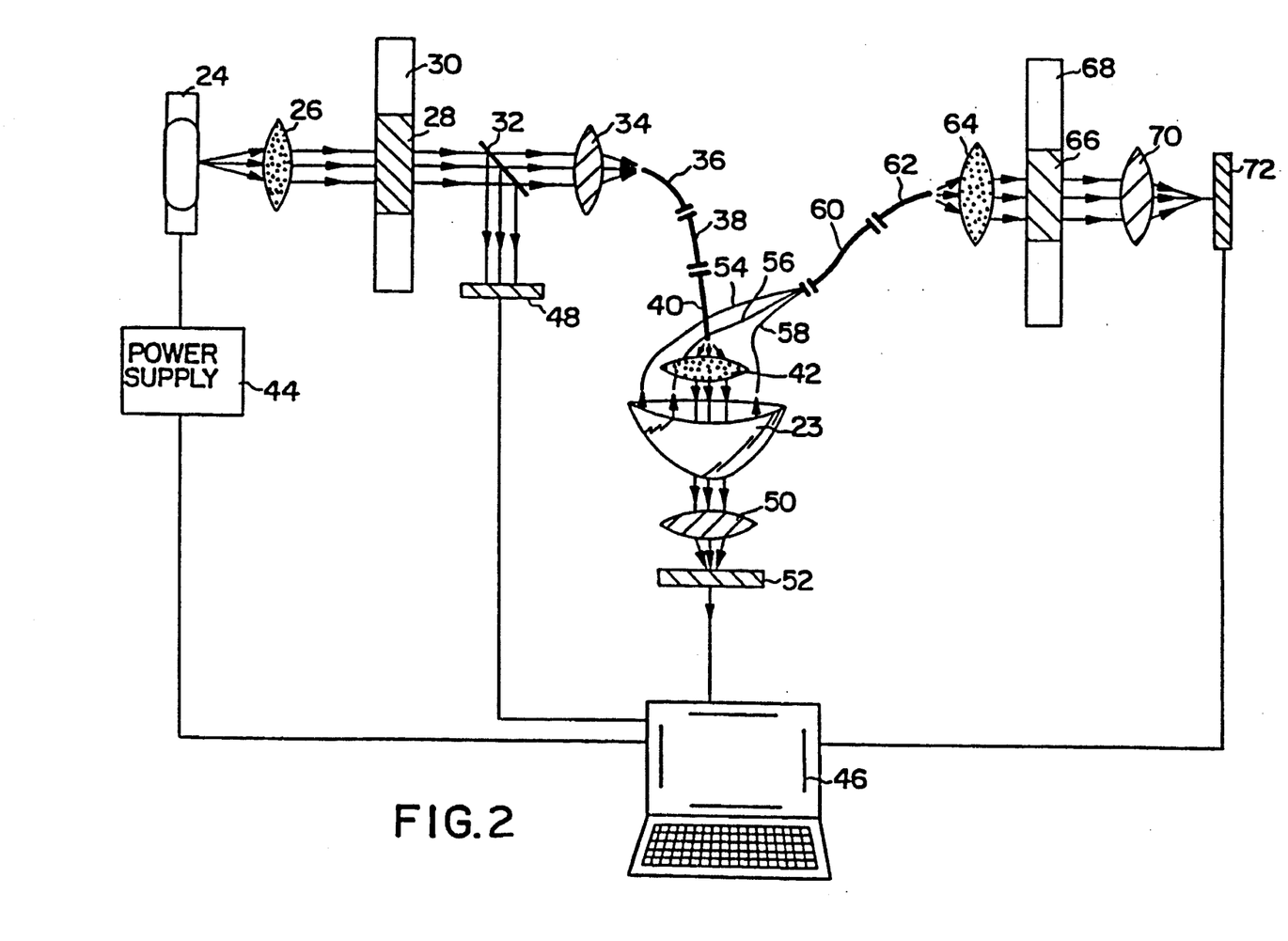
FIG. 2 is a schematic representation of an optical system utilized by the photometer of FIG. 1.

The optical system of the apparatus, described in reference to FIGS. 1 and 2, has a light-delivering assembly, a light-gathering assembly for absorbance measurements, and a light-gathering assembly for fluorescence and luminescence measurements. The light-delivering assembly includes a light source 24; a collimating lens 26; a plurality of bandpass filters 28, individually selectable by means of a rotary filter wheel 30; a beam splitter 32; a focusing lens 34; optical fibers 36, 38, and 40 arranged in series; and a collimating lens 42. Light source 24 typically comprises a xenon arc lamp, energized by a DC power supply 44, e.g., of Type 5 manufactured by Mimir Corporation of Sunnyvale, Calif. The power supply is controlled by a microcomputer 46, which also governs the positioning operations of table 20 and the functions of the optical system, e.g., the angular position of filter wheel 30. Microcomputer 46 may have, for example, a 80286 microprocessor from Intel Corporation of Santa Clara, Calif.

The light-gathering assembly for absorbance measurements comprises a reference-signal photodetector 48, a focusing lens 50, and a second scanning element for collecting light transmitted through microplate 22, e.g., a photodetector 52. Photodetectors 48 and 52, which convert electromagnetic radiation into electric current, may be implemented as photovoltaic cells. After being converted to a digital format by an analog-to-digital converter (not shown), the outputs of photodetectors 48 and 52 are analyzed by microcomputer 46.

The light-gathering assembly for fluorescence and luminescence measurements includes optical pick-up fibers 54, 56, and 58, arranged side-by-side. The pick-up fibers are collectively coupled to a light-transmitting fiber 60, which interfaces with an optical fiber 62. Upon exiting fiber 62, light passes through a collimating lens 64; one of a plurality of bandpass filters 66, selectable by turning a rotary filter wheel 68, which is computer-controlled; and a focusing lens 70. Lens 70 focuses the optical signal on a photodetector 72, whose output is then digitized and processed by microcomputer 46.

In an alternative embodiment of the optical system (FIG. 3), a light-dispersing device 74 replaces filter wheel 68 for fluorescence and luminescence measurements. Moreover, instead of being directed to photodetector 52, the optical signal, transmitted through one of a multiplicity of microplate wells 23, is channeled to the light-dispersing device through lens 50 via sequentially coupled optical fibers 76, 78, and 80. Light-dispersing device 74 comprises a diffraction grating that disperses incoming optical radiation into component wavelengths, which are gathered at photodetector 72. Thus, analyses of optical signals resulting from phenomena of absorbance, fluorescence, and luminescence can be performed over a range of wavelengths, rather than at a narrow spectral bandwidth provided by an individual filter. Consequently, valuable additional information may be learned about the properties of analyte samples being studied.

MOVABLE ARM FOR ROUTING OPTICAL FIBERS

Figure 4:
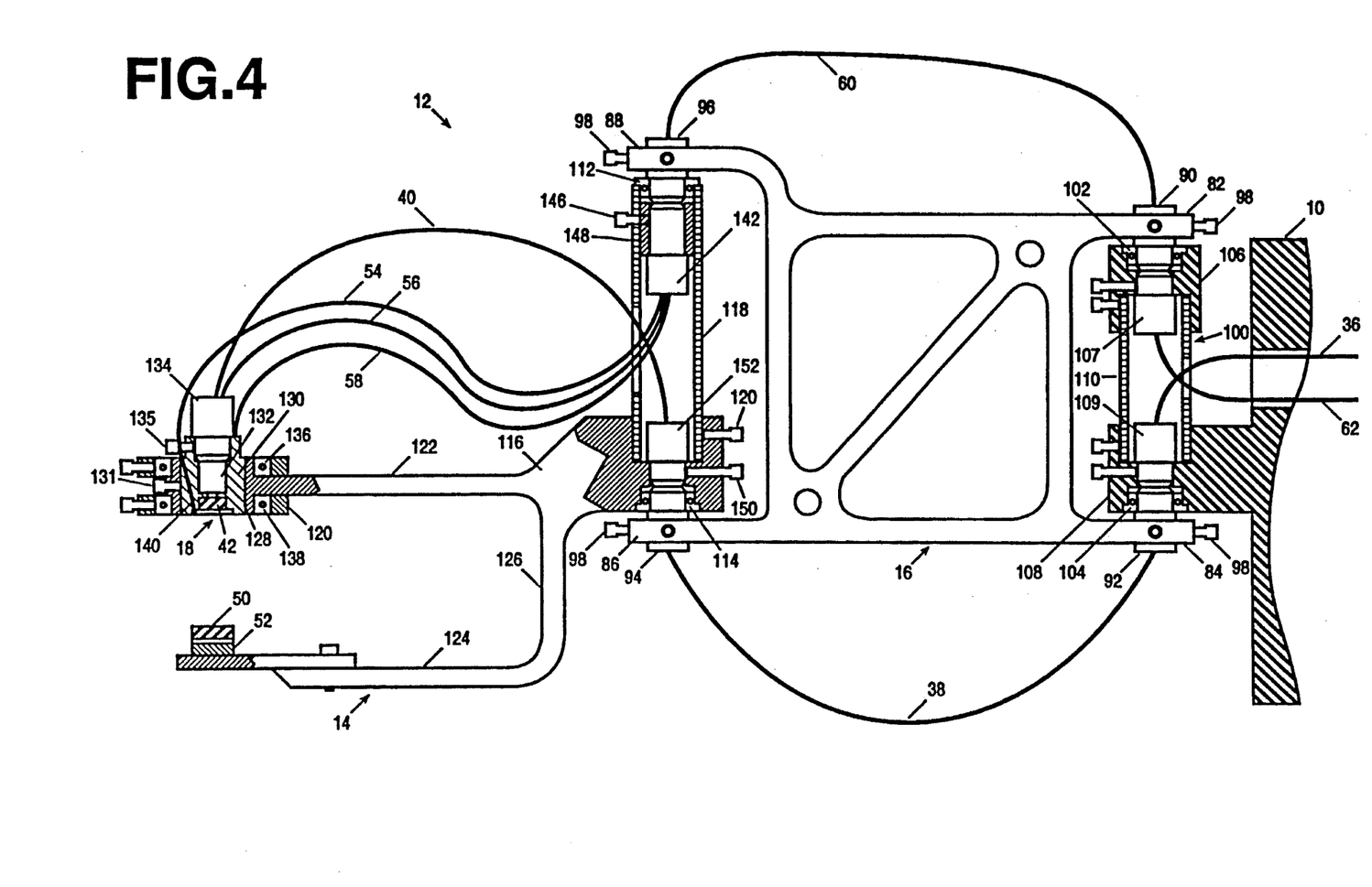
FIG. 4 is a side elevational view of a movable arm of the photometer illustrated in FIG. 1.

Movable arm 12, generally illustrated in FIG. 1, is shown in greater detail in FIG. 4. The arm comprises an articulated linkage having movably coupled members 14 and 16. Member 16 is a substantially rectangular structure having mounting protrusions 82, 84, 86, and 88. The protrusions contain openings accommodating optical-fiber couplers 90, 92, 94, and 96, respectively. The couplers are fixed inside the openings with threaded fasteners, e.g., set screws 98.

Figure 5:
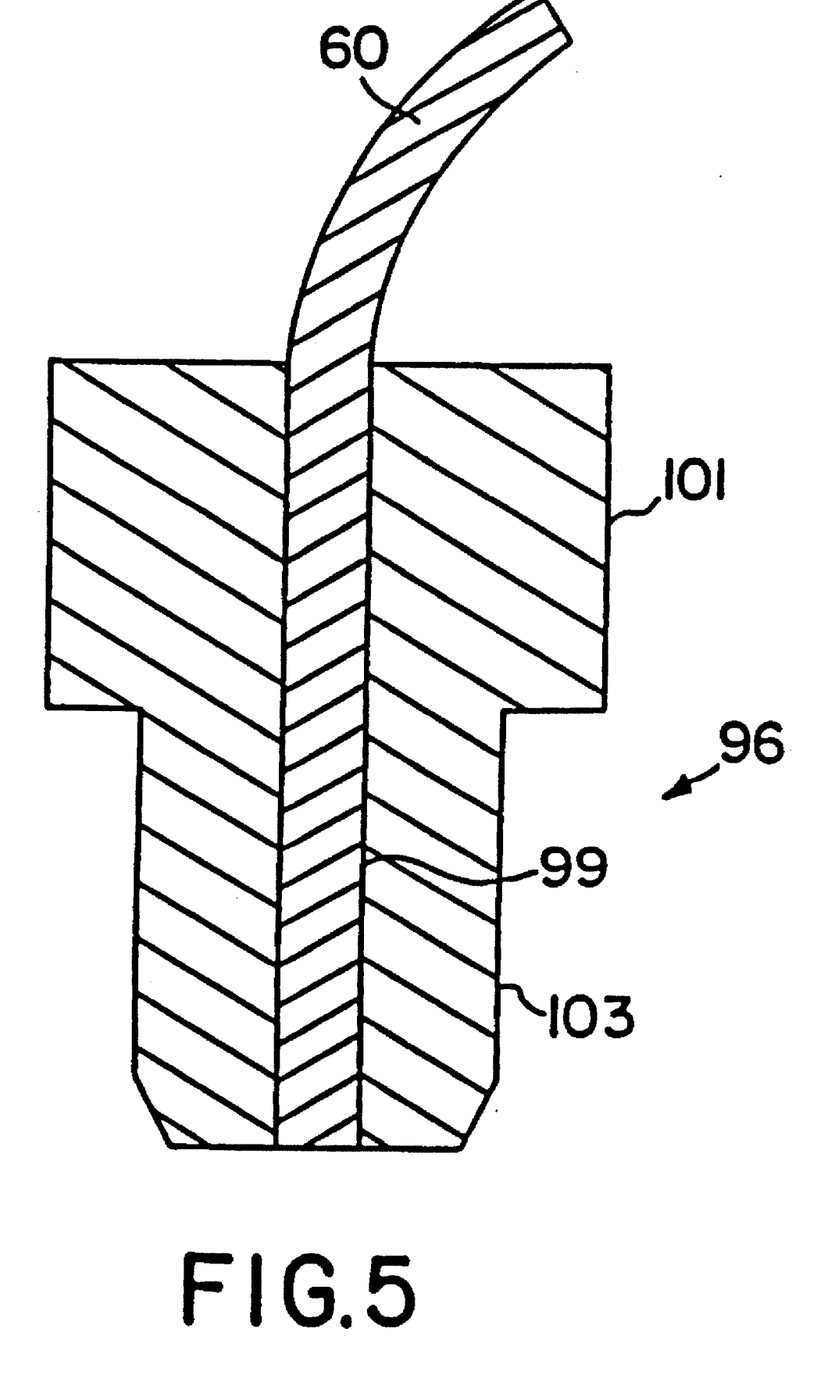
FIG. 5 is a sectional view of an optical-fiber coupler of the photometer of FIG. 1.

As shown in FIG. 5, each of the couplers of the type described above, for example coupler 96, contains a centrally-disposed through bore 99, having a radial dimension that is uniform along the entire length of the bore. Moreover, each coupler has two distinct cylindrical surfaces 101 and 103. Surface 101 has a larger radial dimension then surface 103 and defines the end of the coupler where an optical fiber is to be inserted.

FIG. 4 further illustrates the pivotal attachment of member 16 to housing 10 by means of a bearing assembly 100, which includes a pair of ring bearings 102 and 104 that support couplers 90 and 92. Bearings 102 and 104 are retained within collars 106 and 108, respectively, where collar 108 is integral with housing 10. The two collars are rigidly interconnected by a hollow cylindrical sleeve 110. The above-described structure allows member 16 to pivot with respect to housing 10 about an axis defined by the vertical symmetry axis of sleeve 110.

Similarly, bearings 112 and 114 allow member 16 to pivotally support C-shaped member 14. The C-shaped member has a hinge portion 116, which is rigidly attached to one end of a cylindrical hollow sleeve 118 with a set screw 120. The inner races of bearings 112 and 114 are mounted on couplers 96 and 94, respectively. The outer race of bearing 114 sustains portion 116, while bearing 112 is inserted into the second end of sleeve 118. This structure permits member 14 to pivot with respect to member 16 about an axis defined by the vertical symmetry axis of sleeve 18.

Member 14 further includes parallel beams 122 and 124, integrally connected by a shank 126. Beam 122 contains a cylindrical bore 128 that accommodates scanning head 18 (first scanning element) whereas beam 124 bears the second scanning element comprising lens 50 and photodetector 52. The second scanning element, which is collinear with the scanning head, is located with respect to beam 124 with dowel pins (not shown) and is attached to the beam with screw-type fasteners.

Head 18 comprises a substantially cylindrical casing 130 that is retained inside bore 128, e.g., with a set screw 131. Casing 130 has a through longitudinal opening 132 that houses an optical-fiber coupler 134 at one end and lens 42 at the other. A set screw 135 anchors coupler 134 within opening 132. Ring bearings 136 and 138 are mounted on flanges defining bore 128 for rotationally coupling head 18 to positioning table 20 (schematically shown in FIG. 1). Casing 130 further comprises three through cavities 140 (only one of which is shown in FIG. 4), symmetrically arranged around opening 132 and having an angle of approximately 12° with respect to the vertical axis of the casing.

Cavities 140 contain ends of optical fibers 54, 56, and 58, which may be used to pick up fluorescent emissions. Due to the oblique arrangement of cavities 140, these fibers are less likely to receive excitation from fiber 40. The opposite ends of fibers 54, 56, and 58 are routed via a lateral opening in sleeve 118 into an optical-fiber integrator 142, which contains a through central opening for housing the fibers. Integrator 142 is anchored by a set screw 146 inside a through central bore of spacer 148, the latter being fixed by the same screw within sleeve 118. The integrator is positioned such that its central opening is collinear with the central bore of coupler 96 to allow exchange of radiant energy between fiber 60 and fibers 54, 50, and 56.

Figure 5A:
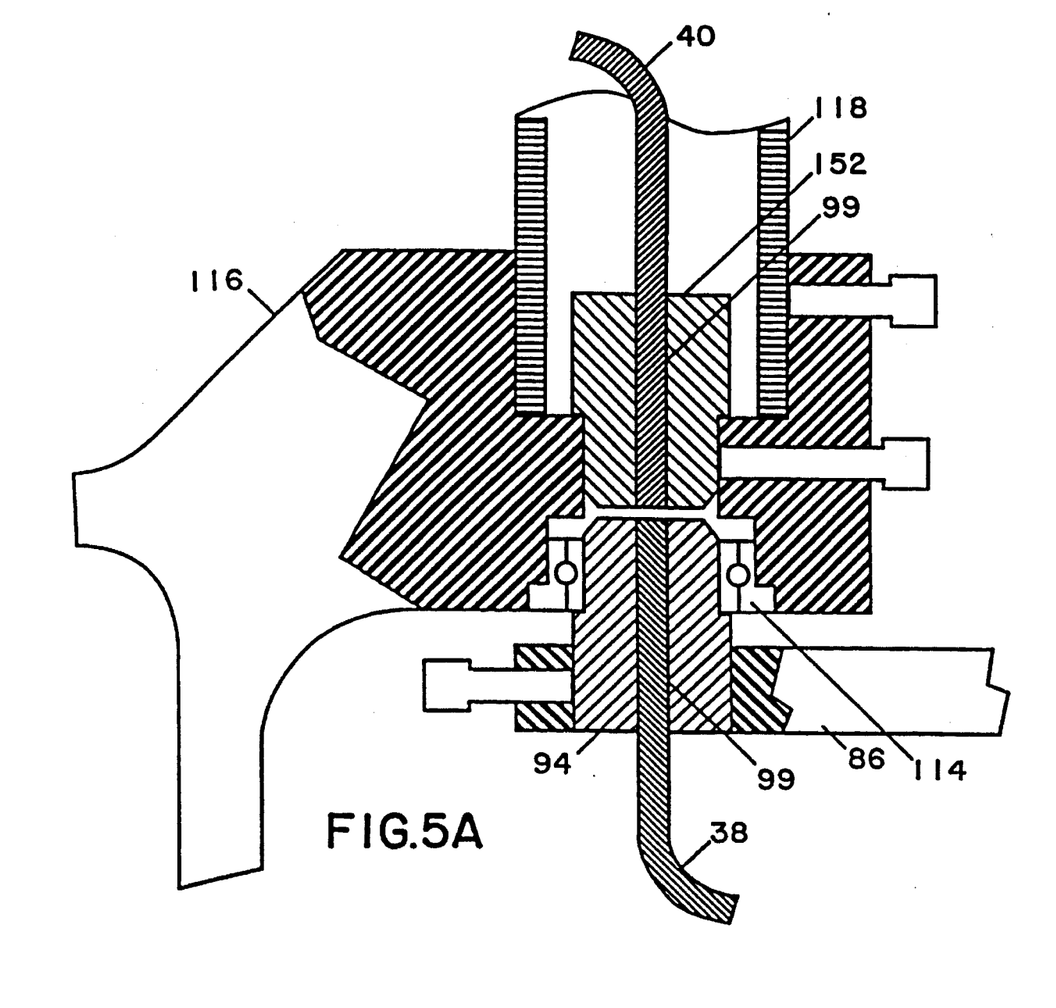
FIG. 5A is a sectional view of an optical-fiber coupling provided by the couplers such as the one shown in FIG. 5.

A set screw 150 secures an optical-fiber coupler 152, identical to couplers 90, 92, 94, 96, and 134, within a through opening in hinge portion 116 such that the bores of couplers 94 and 152 are collinear. The above-described couplers may be made of an opaque material, such as aluminum. Each coupler is about 6.1 mm long and the radial dimension of the longitudinal central bore is approximately 0.5 min. The optical fibers inserted inside the couplers, e.g., couplers 94 and 152, completely occupy central bores 99 such that the ends of the fibers are flush with the end-faces of the couplers, as shown in FIG. 5A. The fibers are typically retained inside the couplers by friction or with an adhesive placed along the fiber shafts such that during insertion of the fibers into the couplers the end-faces of the fibers are not covered with the adhesive.

Figure 6:
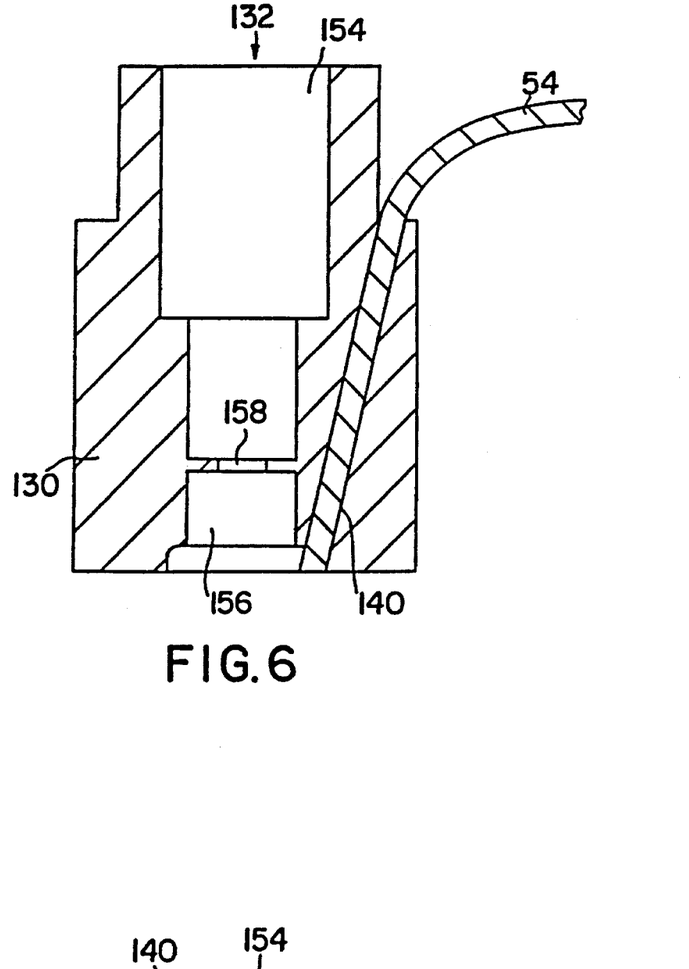
FIG. 6 is a sectional view of an optical scanning head of the photometer shown in FIG. 1.
Figure 7:
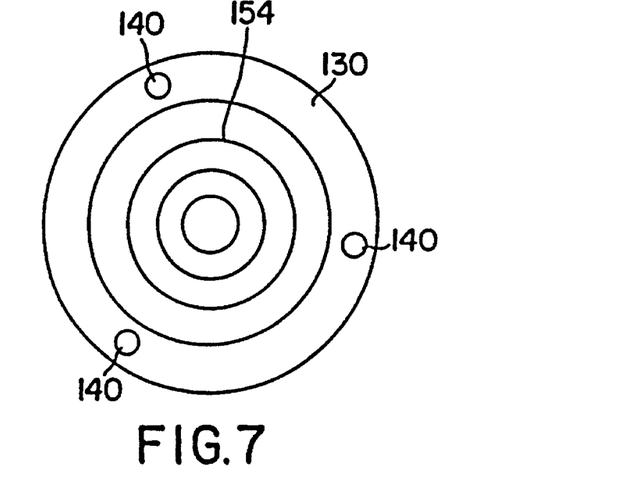
FIG. 7 is a top plan view of the scanning head of FIG. 6.

Casing 130 of scanning head 18 is illustrated in greater detail in FIGS. 6 and 7. A sectional view of the casing (FIG. 6) depicts the configuration of opening 132, which comprises a coupler portion 154 and a lens portion 156. Portion 154 houses coupler 134 (shown in FIG. 4) while portion 156 is used for mounting collimating lens 42 (shown in FIGS. 1 and 4). The path of radiant energy through the casing is restricted by a neck aperture 158 formed in casing 130. Inclined, through cavities 140, only one of which can be shown in the sectional view of FIG. 6, surround opening 132. The cavities contain optical fibers, such as fiber 54, and are equidistant from each other (FIG. 7). The fibers occupy the full length of cavities 140 such that the ends of the fibers are flush or only slightly recessed with respect to the endface of casing 130. The casing may be made of an opaque material, e.g., aluminum, and is approximately 17.5 mm long. Neck aperture 158 restricts the diameter of the light path to approximately 2.0 mm.

Figure 8:
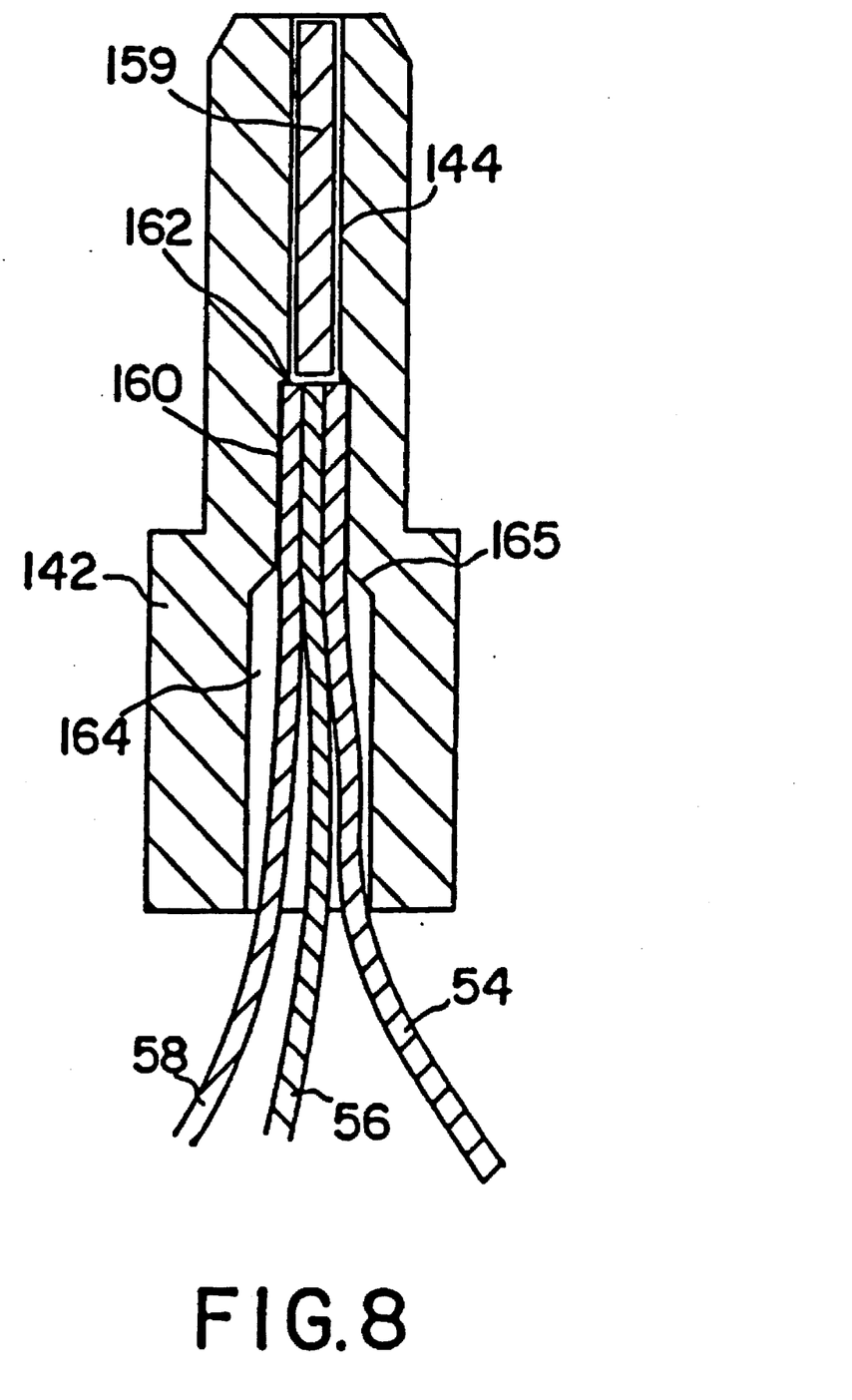
FIG. 8 is a sectional view of an optical-fiber integrator utilized by the photometer of FIG. 1.

The construction of optical-fiber integrator 142 is described in detail with reference to FIG. 8. Integrator 142 has a generally cylindrical shape and a centrally-disposed aperture 144 containing an optical fiber segment 159 that is secured inside the aperture, e.g., by an adhesive. Segment 159 completely fills aperture 144 such that one end of the segment is flush with the endface of integrator 142. The integrator also possesses a cylindrical bore 160 that accommodates the ends of optical fibers 54, 56, and 58, which are fixed inside the bore. Bore 160 has a slightly greater radius than aperture 144 and is joined therewith at a flange 162 so that fiber segment 159 is contiguous with fibers 54, 56, and 58. To maximize light transmission between fiber segment 159 and fibers 54, 56, and 58, the difference in the radial dimensions of aperture 144 and bore 160 is minimal. Thus, fibers 54, 56, and 58 each have a smaller diameter than segment 159 such that their combined cross-sectional area is approximately the same as that of segment 159. In turn, the diameter of segment 159 is the same as those of fibers 36, 38, 40, 60, and 62. To facilitate the insertion of the optical fibers into the integrator, an opening 164, which possesses a greater radius than the bore, is formed collinearly with the latter. Opening 164 has a countersink 165 for gradually guiding the ends of the optical fibers into bore 160. Integrator 142 may be made of an opaque material, e.g., aluminum. The integrator is about 25 mm long, aperture 144 is about 2.3 mm in diameter, and bore 160 has a diameter of approximately 2.3 mm.

Referring once again to FIG. 4, the coupling of the optical fibers is now further described. One end of fiber 40 is secured inside the bore of coupler 134 while the other end is routed inside coupler 152 via a lateral opening within sleeve 118. Similarly, the ends of fiber 38 are retained inside couplers 92 and 94. Fiber 60 and couplers 90 and 96 are arranged identically. A space of about 0.2 mm is provided between the juxtaposed faces of couplers 94 and 152 as well as between those of coupler 96 and integrator 142 for allowing member 14 of the movable arm to freely pivot with respect to member 16.

To link fibers 38 and 60 with the optical system described in the previous section of the specification, optical fibers 36 and 62, interfacing with the rest of the optical components, are routed into sleeve 110 via a lateral opening therein. The ends of these fibers are supported within couplers 107 and 109 anchored inside collars 106 and 108 such that the fibers 36 and 62 are collinear with fibers 38 and 60, respectively. A distance of approximately 0.2 mm separates the contiguous faces of couplers 90 and 107 as well as the faces of couplers 92 and 109. This permits member 16 to pivot freely with respect to housing 10. Fibers 38, 40, and 60 are approximately 20 cm long and 1.0 mm in diameter. Fibers 54, 56, and 58 each have a diameter of about 0.8 mm and a length of approximately 20 cm. In one embodiment of the invention, all optical fibers are made of quartz, thereby allowing transmission of ultraviolet light.

As noted above, the juxtaposed faces of the respective couplers (e.g., 94 and 152) are aligned such that the ends of their respective fibers are collinear and contiguous to maximize light transmission between the fibers. The alignment of the fibers is illustrated in FIG. 5A.

DYNAMIC OPTICAL-FIBER COUPLING PROVIDED BY MOVABLE ARM

The operation of dynamic optical-fiber couplings provided by arm 12 can now be outlined with reference to FIGS. 4 and 5A.

As table 20 positions scanning head 18 at various wells of the microplate, member 14 pivots on bearings 112 and 114 relative to member 16. In turn, member 16 pivots relative to housing 10 on bearings 102 and 104. Specifically, as member 14 rotates with respect to member 16, fibers 40, 54, 56, and 58 move together therewith without twisting or bending. Optical contact between fiber 40 and fiber 38 is maintained through the dynamic coupling provided by couplers 152 and 94 regardless of the angular relationship between members 14 and 16. Optical contact between fiber 60 and pick-up fibers 54, 56, and 58 is maintained in a similar manner with the use of coupler 96 and integrator 142. Moreover, the integrator allows the system to relay the optical signals of a plurality of fibers into a single fiber, thus providing a simple, yet extremely sensitive optical arrangement for performing fluorescence measurements.

Fibers 38 and 60 are also dynamically coupled with fibers 36 and 62, respectively, since couplers 90 and 92 rotate relative to housing 10 in respective bearings 102 and 104, whereas fibers 36 and 62 remain stationary in couplers 109 and 107, which are anchored to collars 106 and 108 of housing 10.

Thus, bending and twisting of optical fibers is eliminated, guaranteeing repeatability and consistency of measurements and preventing mechanical failure of fiber cores due to cyclical bending stresses. Moreover, since compliance of optical fibers does not affect the movement of scanning head 18, stiffer quartz fibers can now be employed to allow transmission of ultraviolet radiation, which may be useful in certain types of fluorescence measurements. Also, the absence of bending resistance in the fibers permits the positioning table to move the scanning head quickly enough to perform kinetic measurements.

Additionally, parallel beams 122 and 124 of member 14 allow the system to position lens 50 and photodetector 52 collinearly with respect to scanning head 18 so that absorbance measurements (typically done by passing radiant energy from fiber 40 to detector 52 through an analyte sample) can be performed together with fluorescence and luminescence assays. Furthermore, the scanning head orients the ends of optical fibers 54, 56, and 58 obliquely to its longitudinal axis to prevent the fibers from picking up optical noise from the edges of microplate wells during fluorescence and luminescence measurements. Fibers 54, 56, and 58 are designed to pick up (receive) flourescence and luminescence emissions and fiber 40 is designated to provide the excitation light in the case of fluorescence. In this manner, fluorescence and luminescence measurements are taken above the microplate rather than through it.

MOVABLE ARM MODIFIED TO ACCOMMODATE ALTERNATIVE EMBODIMENT OF OPTICAL SYSTEM

Figure 3:
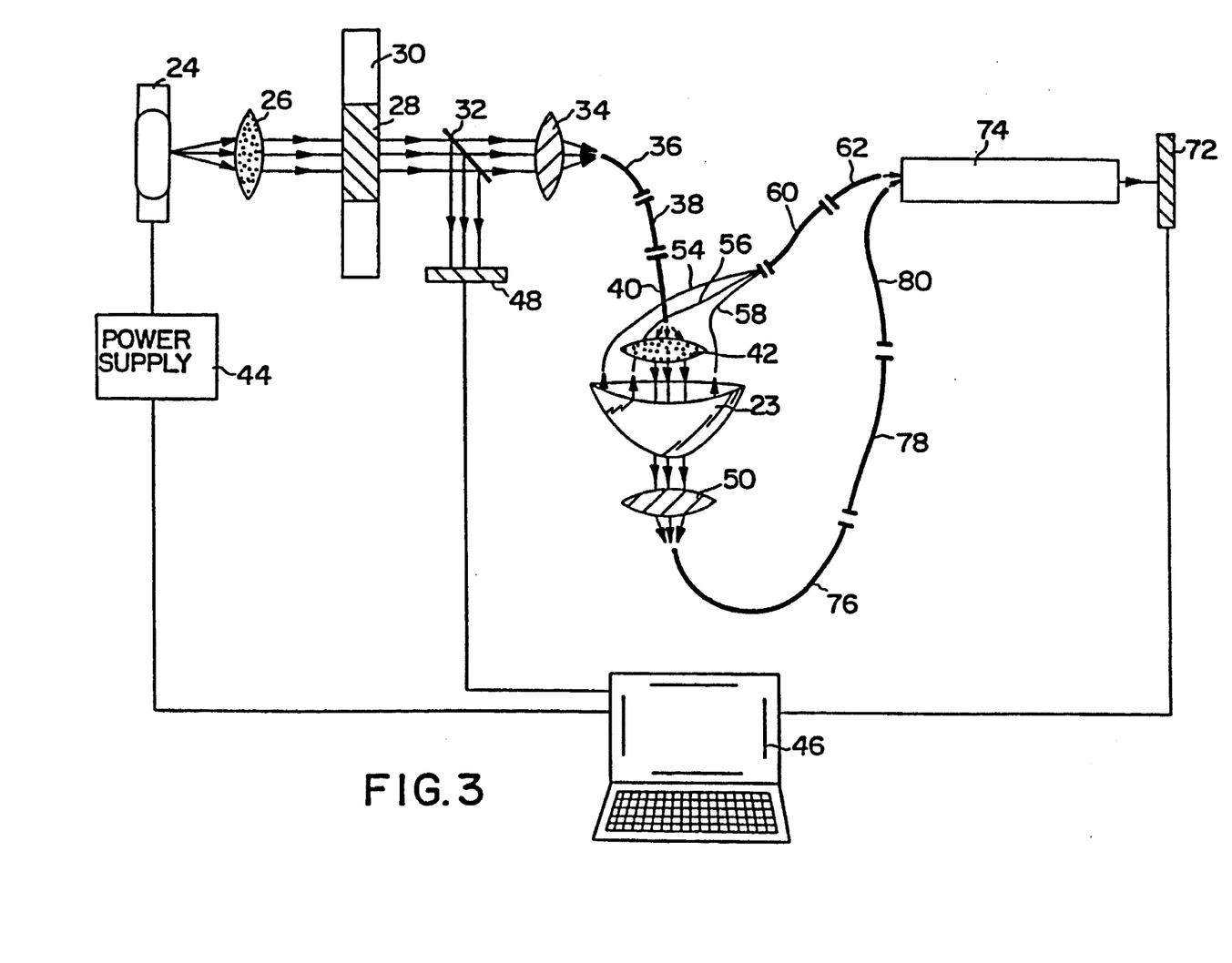
FIG. 3 is a schematic representation of an alternative embodiment of the optical system of FIG. 2.
Figure 9:
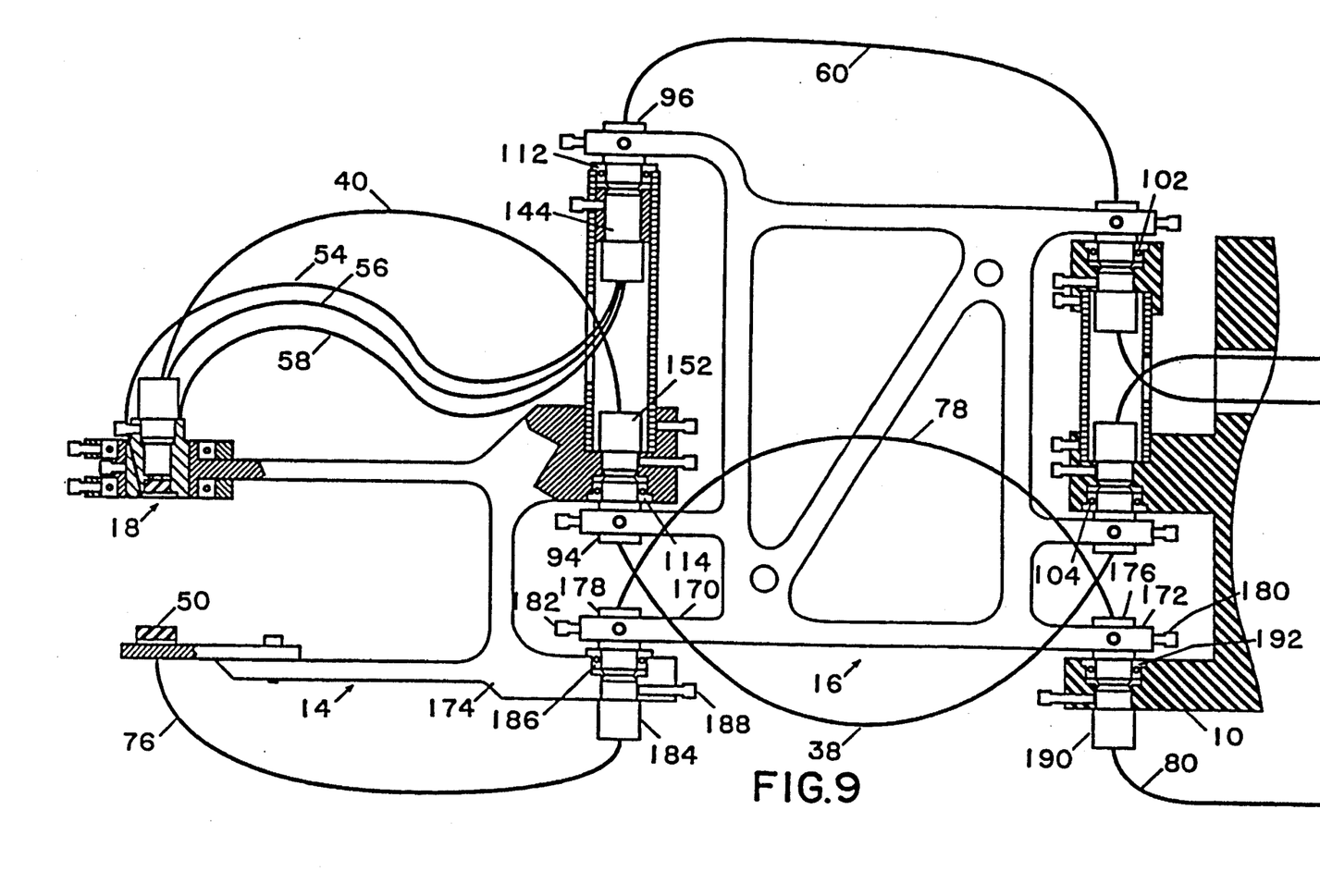
FIG. 9 is a side elevational view of the movable arm of FIG. 4 modified to accommodate the alternative embodiment of the optical system, shown in FIG. 3.

FIG. 9 shows a movable arm modified to accommodate the alternative embodiment of the optical system (illustrated in FIG. 3).

In order to provide an optical connection between the second scanning element, i.e., collimating lens 50, and light dispersing device 74 (FIG. 3), optical fibers 76 and 78 are attached to members 14 and 16, respectively. To accommodate these fibers, mounting protrusions 170 and 172 are added to member 16, whereas member 14 is formed with a second hinged portion 174. Protrusions 170 and 172 have openings for housing optical-fiber couplers 178 and 176, respectively. Couplers 178 and 176 are anchored within their respective openings with set screws 182 and 180 and accommodate ends of fiber 78 in their centrally-disposed through bores.

Hinged portion 174 possesses an opening for housing an optical coupler 184 and a bearing 186. Coupler 184 is positioned such that the through central bores of couplers 178 and 184 are collinear and a distance of about 0.2 mm separates their juxtaposed faces. Bearing 186 houses coupler 178 and, together with bearings 112 and 114, allows member 14 to pivot with respect to member 16. One end of fiber 76 is coupled to lens 50, while the other end is inserted into the bore of coupler 184, which is rigidly attached to member 14 with a set screw 188. As member 14 rotates with respect to member 16, integrator 144 and couplers 152 and 184 rotate together with member 14, whereas couplers 96, 94, and 178 are anchored to member 16 and remain stationary. Thus, member 14 can pivot with respect to member 16 without deforming fibers 76, 40, 54, 56, and 58.

To provide an optical interconnection between fibers 78 and 80, coupler 176 is mated with a coupler 190, which is rigidly attached to housing 10 and is collinear with coupler 190. A bearing 192, mounted in housing 10, supports coupler 176 and, together with bearings 102 and 104, allows member 16 to pivot with respect housing 10 without deforming fibers 38, 60, and 78.

Since lens 50 shares an optical axis with head 18, optically coupling the lens with light dispersing device 74 (FIG. 3) allows the photometer to analyze optical signals, resulting from the phenomenon of absorbance, over a broad range of wavelengths. Thus, a more comprehensive analysis of the analyte samples can be performed.

OPERATION OF PHOTOMETER

Figure 10:
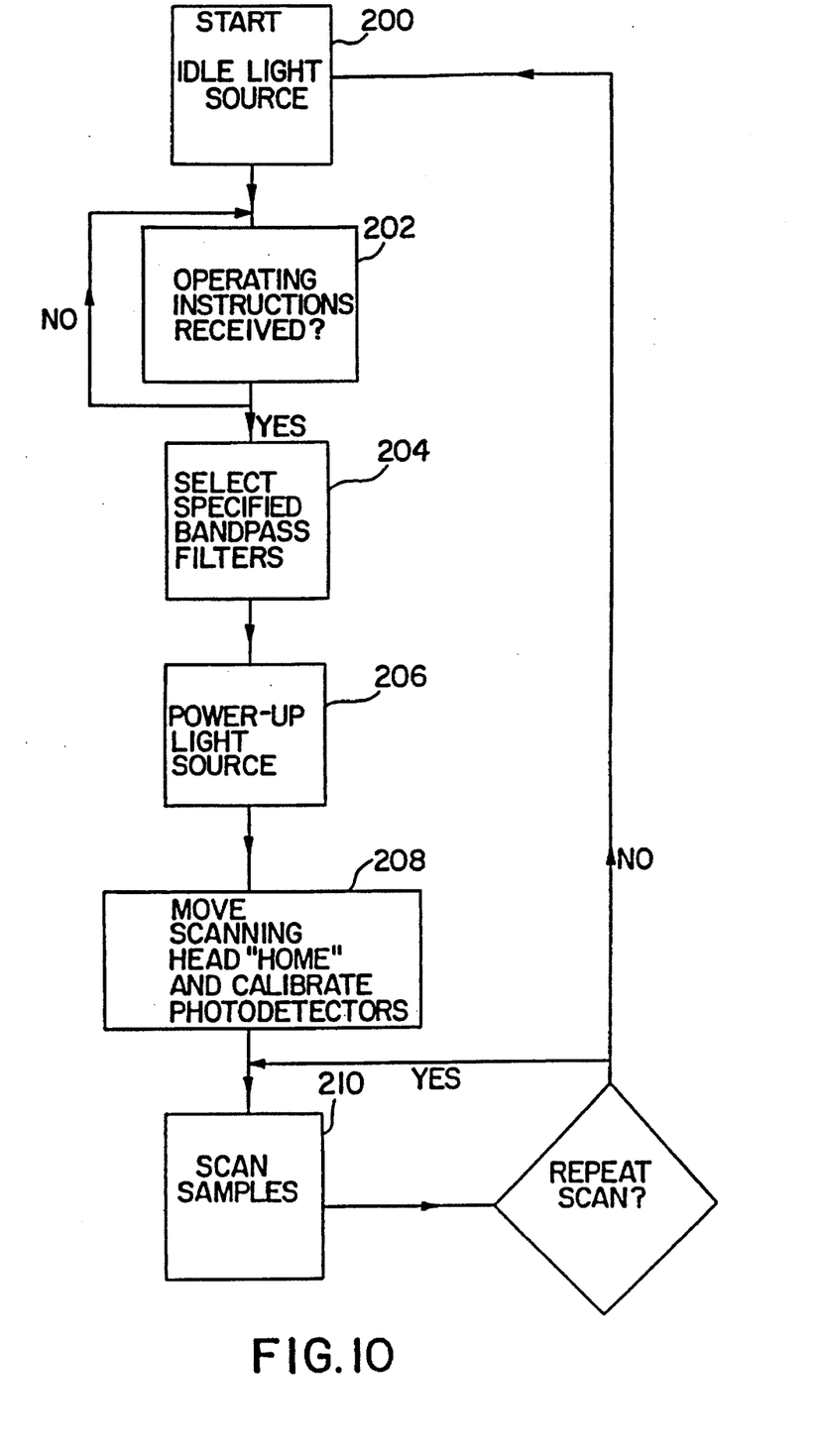
FIG. 10 is a block diagram illustrating the operation of the photometer of FIG. 1.

Operation of the photometer is described in reference to the general steps outlined in FIG. 10 and the apparatus shown in FIG. 1.

As the photometer is initially energized (step 200), microcomputer 46 instructs power supply 44 to maintain light-source 24 in idle mode by applying power of approximately 30 Watts to the light-source.

The microcomputer is then provided with a set of operating instructions (step 202). These contain information regarding specific measurement parameters, e.g., type of scan (absorbance, fluorescence, or luminescence-measured individually or simultaneously), number of times to repeat the scanning cycle, various geometries of microplate-well arrays, filter positions, duration of scanning cycle, etc.

In accordance with the instructions received in step 202, the 18 microcomputer selects appropriate bandpass filters 28 and 66 by rotating filter wheels 30 and 68, respectively (step 204). After the selection of the filters is completed, the microcomputer instructs the power supply to increase power applied to the light source to approximately 75 Watts (step 206).

After the light source has been powered up, the microcomputer directs positioning table 20 to move head 18 to a predetermined "home" position (step 208), where the light path between head 18 and photodetector 52 is unobstructed by microplate 22. Calibration of photodetectors 48 and 52 is then performed for absorbance measurements.

Following photodetector calibration, microcomputer 46 directs table 20 to move head 18 such that samples located in specified wells 23 of microplate 22 are scanned (step 210). As table 20 moves head 18 (typically in a push-pull fashion), it does not interfere with fibers 40, 54, 56, and 58. During a scan, signals of photodetector 72 and/or photodetectors 48 and 52 are processed by the microcomputer to measure one or more of absorbance, fluorescence, and luminescence of the analyte samples.

Depending on the instructions received during step 202, the microprocessor either repeats the scan (step 210) or switches the light source to idle mode (step 200).

Because of the optical coupling provided by movable arm 12, bending and twisting of optical fibers during the scanning procedure is eliminated. Thus, the optical energy path through each fiber remains constant, so that measurements produced during a scan are consistent from sample to sample. Moreover, measurements from one scan to another are fully repeatable. Additionally, since cyclical bending of fibers does not occur, quartz optical fibers can be used to perform spectroscopic analyses in the ultraviolet region of the spectrum.

Thus, it has been shown that we have provided a multi-functional photometer which measures absorbance, fluorescence, and luminescence of a sample; which provides repeatable measurements and produces consistent readings between different test sites; which eliminates recurring bending of optical fibers and mechanical failure thereof; which utilizes optical radiation ranging from the ultraviolet to the infrared spectrum; which is able to carry out kinetic measurements; which can accommodate microplates with different well configurations; and which is relatively simple and inexpensive to manufacture.

Although the multi-functional photometer has been shown and described in the form of specific embodiments, its configurations and materials are given only as examples, and many other modifications of the apparatus are possible. For example, the photodetectors utilized in the optical system may be executed as photoemissive tubes, photomultiplier tubes, photodiodes, etc. A prism, as well as a filter, may be used to disperse light instead of a diffraction grating. Light sources, such as xenon flash lamps, tungsten-halogen lamps, and mercury vapor lamps may be employed with the optical system of the apparatus. Liquid-filled optical fibers may replace glass and plastic fibers. Optical-fiber couplers and integrator may be made of a plurality of opaque materials and may have different configurations. For instance, the optical fiber integrator may accommodate a multiplicity of fibers. Moreover, a coupling with two integrators may be used to optically interconnect two pluralities of fibers. Additionally, an axial positioning scale may take place of the Cartesian-coordinate positioning table. Instead of microplate wells, analyte samples may be placed in membranes or gels. It will also be appreciated that the photometer may be operated without computer control, as in the case of numerous prior-art photometers that do not require such control.

Therefore, the scope of the invention should be determined, not by the examples given, but by the appended claims and their equivalents.

What we claim is:

1. An optical coupling for transferring radiant energy between a first light-transmitting conduit coupled to a first rigid member and a second light-transmitting conduit coupled to a second rigid member, said first and said second light-transmitting conduits having fixed individual shapes, said first rigid member being pivotally attached to said second rigid member at a pivot axis, said optical coupling comprising:

a first coupling element statically connected to said first rigid member, said first coupling element having a first though aperture, said first through aperture being collinear with said pivot axis and accommodating one end of said first light-transmitting conduit; and a second coupling element statically connected to said second rigid member, said second coupling element having a second through aperture, said second through aperture being collinear with said pivot axis and accommodating one end of said second light-transmitting conduit.

2. The optical coupling of claim 1 wherein said first and said second coupling elements have facing surfaces separated by a gap for permitting said first and said second light-transmitting conduits to exchange said radiant energy and for allowing said first and said second rigid members to pivot with respect to each other.

3. The optical coupling of claim 2 wherein said first and second light-transmitting conduits are optical fibers.

4. An optical coupling for transferring radiant energy between a first light-transmitting conduit coupled to a first rigid member and a plurality of second light-transmitting conduits coupled to a second rigid member, said plurality of second light-transmitting conduits having distal and proximal ends, said first light-transmitting conduit and said plurality of second light-transmitting conduits having fixed individual shapes, said first rigid member being pivotally coupled to said second rigid member at a pivot axis, said optical coupling comprising:

a first coupling element statically connected to said first rigid member, said first coupling element having a first through aperture, said first through aperture being collinear with said pivot axis and accommodating one end of said first light-transmitting conduit; and a second coupling element statically connected to said second rigid member, said second coupling element having a second through aperture, said second through aperture being collinear with said pivot axis and accommodating proximal ends of said plurality of second light-transmitting conduits.

5. The optical coupling of claim 4 wherein said first and said second coupling elements have facing surfaces separated by a gap for permitting said first light-transmitting conduit and said plurality of second light-transmitting conduits to exchange said radiant energy and for allowing said first and said second rigid members to pivot with respect to each other.

6. The optical coupling of claim 5 wherein said light-transmitting conduits comprise optical fibers.

7. The optical coupling of claim 5 wherein said plurality of second light-transmitting conduits is three.

8. An apparatus for optically coupling a plurality of optical fibers with a single optical fiber, said apparatus comprising an opaque member having a through aperture for housing ends of said plurality of optical fibers, said through aperture also housing an optical-fiber segment contiguous with said ends of said plurality of optical fibers, said optical-fiber segment being collinear and contiguous with said single optical fiber such that said optical-fiber segment defines an optical path between said plurality of optical fibers and said single optical fiber.

9. An optical coupling as in claim 1 wherein said first rigid member and said second rigid member are capable of moving in space relative to each other, while said first and said second light-transmitting conduits maintain said fixed individual shapes.

10. An apparatus as in claim 8 wherein said single optical fiber is separated from said plurality of fibers by a gap.

* * * * *